(12) United States Patent
Eng et al.

(10) Patent No.: US 8,723,949 B2
(45) Date of Patent: May 13, 2014

(54) FISH ACTIVITY MONITORING SYSTEM FOR EARLY WARNING OF WATER CONTAMINATION

(75) Inventors: How Lung Eng, Singapore (SG); Beng Hai Lee, Singapore (SG); Suryanti Yunita Anggrelly, Singapore (SG); Boon Fong Chew, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 346 days.

(21) Appl. No.: 12/936,716

(22) PCT Filed: Apr. 9, 2009

(86) PCT No.: PCT/SG2009/000133
§ 371 (c)(1),
(2), (4) Date: May 27, 2011

(87) PCT Pub. No.: WO2009/126116
PCT Pub. Date: Oct. 15, 2009

(65) Prior Publication Data
US 2012/0086802 A1    Apr. 12, 2012

(51) Int. Cl.
*H04N 7/18* (2006.01)
*C02F 1/00* (2006.01)
*G01N 33/18* (2006.01)

(52) U.S. Cl.
CPC .............. *C02F 1/00* (2013.01); *G01N 33/186* (2013.01)
USPC ...................................................... 348/135

(58) Field of Classification Search
USPC ............. 348/135; 119/228; 382/103; 702/71; 43/4
See application file for complete search history.

(56) References Cited

U.S. PATENT DOCUMENTS

| | | | |
|---|---|---|---|
| 4,626,992 A | 12/1986 | Greaves et al. | |
| 4,888,703 A | 12/1989 | Baba et al. | |
| 5,222,458 A | 6/1993 | Pippy | |
| 5,588,245 A * | 12/1996 | Vance | 43/25.2 |
| 5,816,196 A * | 10/1998 | Webster et al. | 119/228 |
| 5,841,884 A | 11/1998 | Yamamoto | |
| 5,903,305 A | 5/1999 | Yamamoto | |
| 6,393,899 B1 * | 5/2002 | Shedd et al. | 73/61.41 |
| 6,988,394 B2 * | 1/2006 | Shedd et al. | 73/61.41 |
| 8,423,333 B2 * | 4/2013 | Maegawa et al. | 703/6 |

(Continued)

FOREIGN PATENT DOCUMENTS

| JP | 2242154 | 9/1990 |
|---|---|---|
| JP | 7-63747 | 3/1995 |

(Continued)

OTHER PUBLICATIONS

International Patent Application No. PCT/SG2009/000133: International Search Report dated May 29, 2009, 4 pages.

(Continued)

*Primary Examiner* — Nhon Diep
(74) *Attorney, Agent, or Firm* — Baker & Hostetler LLP

(57) ABSTRACT

A system and system for monitoring water quality. The system comprises a container for receiving a flow of water to be monitored, the container containing a plurality of fish and configured such that a substantially 3-dimensional group behavior of the fish is accommodated; a first imaging device disposed above the container for obtaining top view video data of the fish; and means for identifying individual fish based on foreground object detection.

25 Claims, 15 Drawing Sheets

(56) References Cited

U.S. PATENT DOCUMENTS

| | | |
|---|---|---|
| 2004/0085443 A1* | 5/2004 | Kallioniemi et al. ......... 348/135 |
| 2004/0243328 A1* | 12/2004 | Rapp et al. ...................... 702/71 |
| 2007/0220798 A1* | 9/2007 | Davidson ............................. 43/4 |
| 2008/0306980 A1* | 12/2008 | Brunner et al. ............... 707/102 |

FOREIGN PATENT DOCUMENTS

| | | | |
|---|---|---|---|
| JP | 7-37975 | 4/1995 | |
| JP | 11-142394 | 5/1999 | |
| JP | 2002257815 A * | 9/2002 | ............ G01N 33/18 |
| JP | 2005-150840 | 6/2005 | |
| JP | 2007-85828 | 4/2007 | |
| JP | 2007085828 A * | 4/2007 | |
| WO | WO 2009/126116 | 10/2009 | |

OTHER PUBLICATIONS

Eng et al., "Robust human detection within a highly dynamic aquatic environment in real time", IEEE Transactions on Image Processing, Jun. 2006, 15(6), 1583-1600.

Frost and Sullivan Research Service, "U.S. drinking water homeland security technologies—strategy study of an emerging market", www.frost.com, #F063-15, Jun. 2005, 84 pages.

bbe Moldaenke, "bbe fish toximeter: a powerful instrument for water toxicity monitoring", http://www.bbe-moldaenke.de/home/fish-toximeter/, available Apr. 4, 2008, 2 page brochure.

* cited by examiner

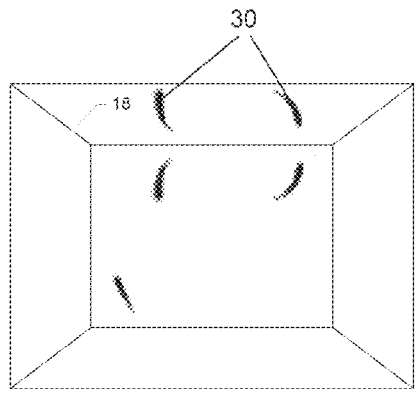 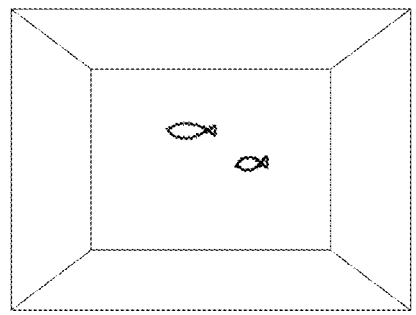
Figure 3(a)　　　　　　　Figure 3(b)
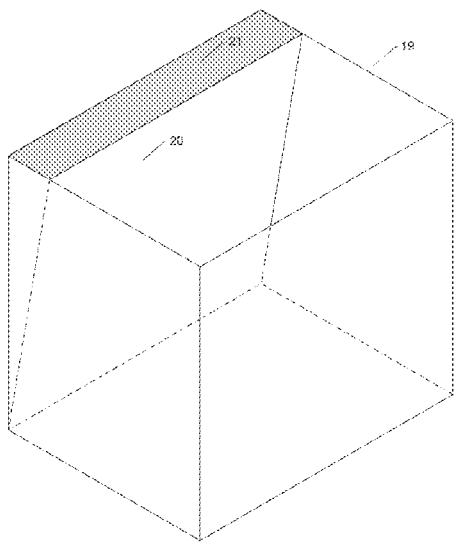
Figure 3(c)
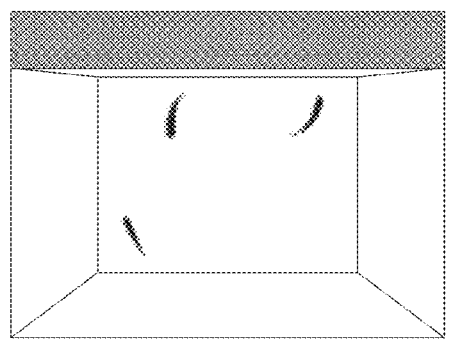
Figure 3(d)

FISH ACTIVITY MONITORING SYSTEM FOR EARLY WARNING OF WATER CONTAMINATION

CROSS-REFERENCE TO RELATED APPLICATIONS

This application is the National Stage of International Application No. PCT/SG2009/000133 filed Apr. 9, 2009, which claims the benefit of U.S. application No. 61/043,473, filed Apr. 9, 2008, the disclosures of which are incorporated herein by reference in their entirety.

FIELD OF INVENTION

The present invention relates generally to a system and method for monitoring water quality.

BACKGROUND

In water treatment and supply, it may be desirable, e.g. for security reasons, to regularly monitor the water for contamination. One method that is rapidly gaining prominence in such drinking water security applications comprises the use of living organisms or enzymatic reactions as toxicity indicators. By monitoring adverse biological effects on test organisms, it is possible to confirm the presence of toxins in the water supply prior to performing further analysis to determine the exact nature of the threat. The key advantages of using bio-monitoring are its rapid response and its ability to be used at critical locations, such as at the downstream of a water distribution system, prior to biological processing in a waste-water treatment plant. There are several different organisms that can be used to monitor for toxicity including e.g. bacteria, invertebrates and fish.

In early systems, such monitoring of the status of the test organisms is carried out by human inspectors. It has been noted that manual monitoring round-the-clock is tedious and subject to error since human alertness may degrade after a prolonged period, while periodic monitoring does not provide real-time information for appropriate responses. A computer vision system may be more suitable in this situation as the machine can provide constant monitoring over a long period of time at the same level of performance.

In one prior art approach, a video camera is used to visually monitor the movements of the fish. A behavioral model based on a set of statistical distributions of pre-selected movement parameters is computed as a time function. The approach further comprises comparing observed movement statistical distribution with a set of prediction parameters, and generating a warning message when the fish' observed movements do not correspond to prediction parameters. However, as the prediction parameters are dependent on the previously observed behavior, this approach may not be responsive to situations subject to different types of fish and different contaminant exposures that have not been observed and recorded in the historical database.

In another prior art approach, a monitoring area is divided into a plurality of small blocks (i.e. sensing points) in rows and columns and the luminance value of each block is checked to determine whether the block is occupied by a fish or not. The blocks being occupied by a fish are labeled such that an analysis of fish action pattern may be performed by calculating the number of labeled blocks, moving speed, etc. In this approach, the fish tank needs to be divided into a number of confinement structures, each containing one fish. As a result, the action pattern may not be accurate as compared to a natural setting in which a plurality of fish may swim in a group.

In one existing system, water is passed through a transparent tank having a substantially narrow width, and containing a plurality of fish. A video camera is directed toward the front side of the tank, i.e. the larger side defined by the length and height of the tank. The system measures behavioral parameters such as speed, behaviors (e.g. in terms of height in tank, turns and circular motion), size and number of active fish. Toxicity is measured as global statistics of these behavioral parameters. However, the system is not able to resolve occlusions, i.e. situations where one fish is partially or fully obstructed by one or more fish positioned nearer to the camera. As the analysis of fish activity is based on global motion statistics, the analysis may be inconclusive in instances with just one or two dead fish. In addition, due to the very narrow width, it is not a natural setting for keeping the fish. This could lead to the fish not being able to move sufficiently fast, thus may be detected as dead fish, resulting in false alarms.

Another existing water quality monitoring system comprises a receiving tank and a monitoring tank, which may have up to two sections, each containing one fish. A picture signal from a video camera positioned at one side of the monitoring tank is inputted into a fish detecting sensor where the picture signal is processed to continuously detect the position of the fish. A position signal is fed into a computer for determining the actional pattern of the fish, which is then compared with a fish abnormal actional pattern stored in advance to check whether the actional pattern observed is abnormal or not. However, like the above approaches, the number of fish being monitored is limited, and the actional pattern may not be accurate as compared to a natural setting in which a plurality of fish may swim in a group.

A need therefore exists to provide a system and method for monitoring water quality that seek to address at least one of the above problems.

SUMMARY

In accordance with a first aspect of the present invention there is provided a system for monitoring water quality, the system comprising a container for receiving a flow of water to be monitored, the container containing a plurality of fish and configured such that a substantially 3-dimensional group behaviour of the fish is accommodated; a first imaging device disposed above the container for obtaining top view video data of the fish; and means for identifying individual fish based on foreground object detection.

The system may further comprise a second imaging device disposed on a side of the container for obtaining side view video data of the fish.

The system may further comprise a confinement structure disposed within said container, the confinement structure comprising a substantially continuous perimeter wall for accommodating the fish therein, wherein said confinement structure is dimensioned for accommodating the substantially 3-dimensional group behaviour of the fish.

The perimeter wall may be configured such that it approximates a field of view of said first imaging device.

The perimeter wall may be substantially translucent.

A portion of the perimeter wall facing said second imaging device may be substantially transparent, while a remaining portion of the perimeter wall is substantially translucent.

The confinement structure may further comprise a substantially opaque cover member disposed to cover the substantially transparent portion of the perimeter wall for reducing reflection of the fish in said top view video data.

The system may further comprise a lighting apparatus configured to provide substantially even background light for the first imaging device.

The lighting apparatus may comprise a light source disposed underneath the container and means for diffusing light from the light source disposed between the light source and the container.

The system may be configured to minimize external light from entering the system during operation.

The means for identifying individual fish may be arranged for resolving clustered foreground objects.

Resolving clustered foreground objects may comprise performing hierarchical k-means clustering to fit k-number of ellipses into each contiguous blob in a silhouette map of the top view image data, k=1, 2, 3, . . . ; determining a best k based on a minimum validity score for fitting the k-number of ellipses to each blob.

The system may further comprise means for determining a number of inactive fish.

The system may further comprise means for applying a stimulus to the fish if the number of inactive fish exceeds a first threshold to reduce false alarms.

The system may further comprise a communication device for sending an alarm signal, the alarm signal being generated if the number of inactive fish exceeds a second threshold after the stimulus has been applied.

The stimulus may comprise a sound.

The system may further comprise means to determine an activity level of the plurality of fish as a group behaviour, the activity level being determined based on one or more of a group consisting of overall group speed, motion trajectory and randomness measure.

The system may further comprise means to determine a group distribution of the fish as a group behaviour.

The system may further comprise means to determine a social interaction of the fish as a group behaviour, the social interaction being determined based on one or more of a group consisting of level of proximity that the fish are swimming to one another, number of clusters formed by the fish and dominance of these clusters.

In accordance with a second aspect of the present invention there is provided a method of monitoring water quality, the method comprising the steps of receiving a flow of water to be monitored in a container, the container containing a plurality of fish and configured such that a substantially 3-dimensional group behaviour of the fish is accommodated; obtaining top view video data of the fish; and identifying individual fish based on foreground object detection.

The method may further comprise performing hierarchical k-means clustering to fit k-number of ellipses into each contiguous blob in a silhouette map of the top view image data, k=1, 2, 3, . . . ; determining a best k based on a minimum validity score for fitting the k-number of ellipses to each blob.

The method may further comprise applying a stimulus to the fish if a number of inactive fish exceeds a first threshold to reduce false alarms.

The method may further comprise determining an activity level of the plurality of fish as a group behaviour, the activity level being determined based on one or more of a group consisting of overall group speed, motion trajectory and randomness measure.

The method may further comprise determining a group distribution of the fish as a group behaviour.

The method may further comprise determining a social interaction of the fish as a group behaviour, the social interaction being determined based on one or more of a group consisting of level of proximity that the fish are swimming to one another, number of clusters formed by the fish and dominance of these clusters.

BRIEF DESCRIPTION OF THE DRAWINGS

Embodiments of the invention will be better understood and readily apparent to one of ordinary skill in the art from the following written description, by way of example only, and in conjunction with the drawings, in which:

FIG. 3(a) shows a top view of a monitoring area using a rectangular confinement structure having a transparent side face according to an example embodiment.

FIG. 3(b) shows a side view of a monitoring area using a rectangular confinement structure having a transparent side face according to an example embodiment.

FIG. 3(c) is a perspective view of the confinement structure of FIG. 3(a) that has been modified to minimize reflection according to an example embodiment.

FIG. 3(d) is a top view of a monitoring area using the confinement structure of FIG. 3(c).

DETAILED DESCRIPTION

Figure 1A:
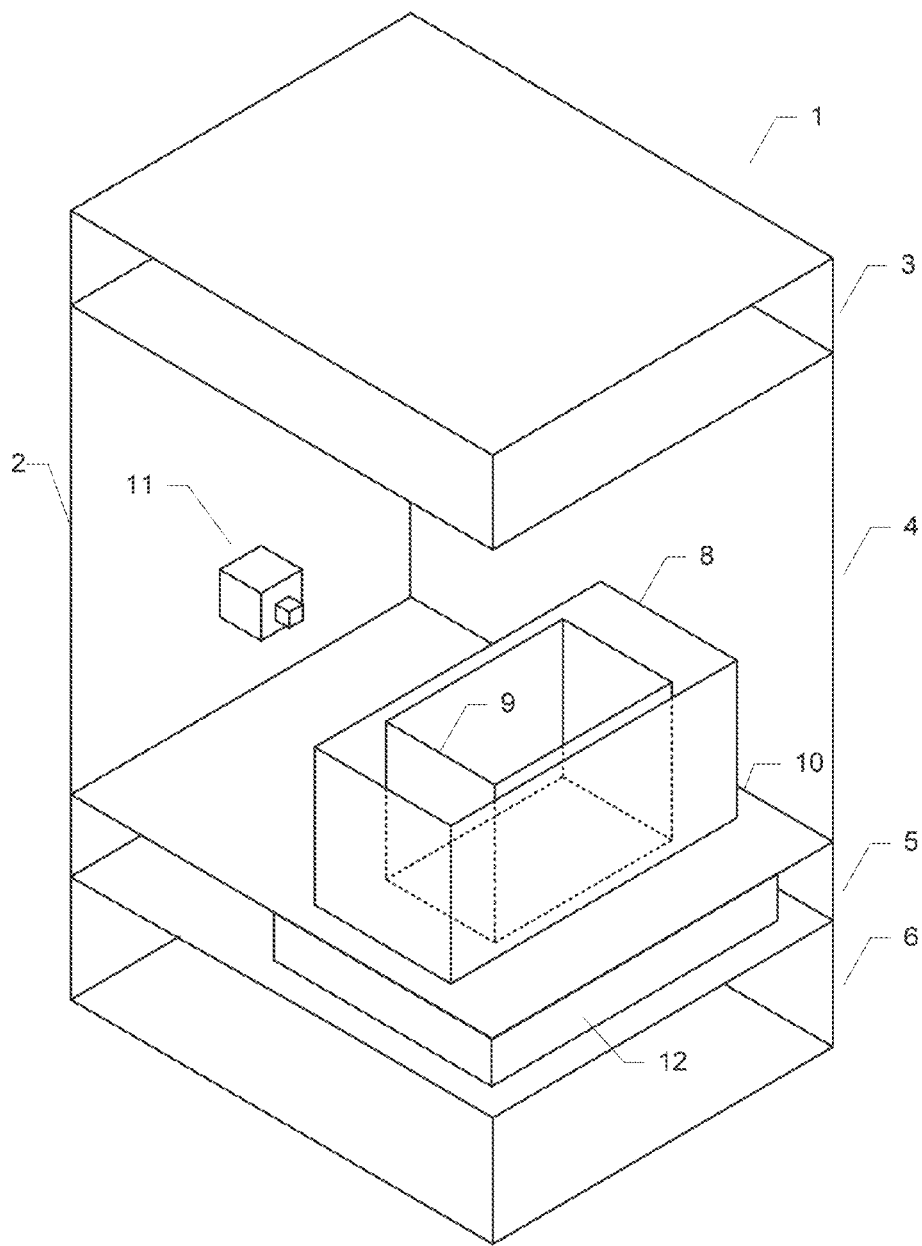
FIG. 1(a) is a perspective view of a system for monitoring water quality according to an example embodiment.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "computing", "detecting", "determining", "counting", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

Figure 8:
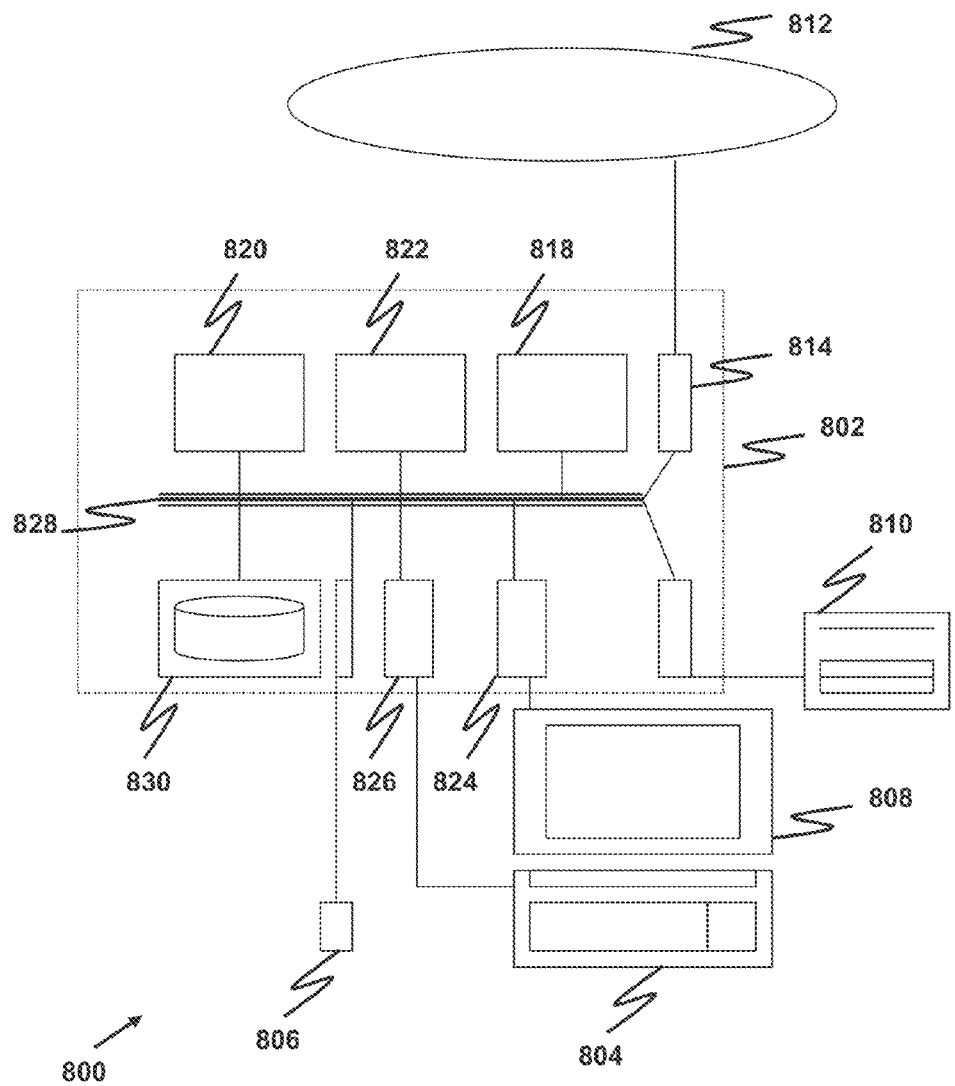
FIG. 8 is a schematic diagram of a computer system according to an example embodiment.

The method and system of the example embodiment can be implemented on a computer system 800, schematically shown in FIG. 8. It may be implemented as software, such as a computer program being executed within the computer system 800, and instructing the computer system 800 to conduct the method of the example embodiment.

The computer system 800 comprises a computer module 802, input modules such as a keyboard 804 and mouse 806 and a plurality of output devices such as a display 808, and printer 810.

The computer module 802 is connected to a computer network 812 via a suitable transceiver device 814, to enable access to e.g. the Internet or other network systems such as Local Area Network (LAN) or Wide Area Network (WAN).

The computer module 802 in the example includes a processor 818, a Random Access Memory (RAM) 820 and a Read Only Memory (ROM) 822. The computer module 802 also includes a number of Input/Output (I/O) interfaces, for example I/O interface 824 to the display 808, and I/O interface 826 to the keyboard 804.

The components of the computer module 802 typically communicate via an interconnected bus 828 and in a manner known to the person skilled in the relevant art.

The application program is typically supplied to the user of the computer system 800 encoded on a data storage medium such as a CD-ROM or flash memory carrier and read utilising a corresponding data storage medium drive of a data storage device 830. The application program is read and controlled in its execution by the processor 818. Intermediate storage of program data may be accomplished using RAM 820.

With reference to FIGS. 1(a)-1(d), a system 1 for monitoring water quality according to an example embodiment is described. System 1 comprises an enclosure unit 2 divided into a top section 3, a middle section 4, a lower middle section 5, and a bottom section 6. The entire system 1 may be covered during operation to prevent any external light from entering it, thereby ensuring consistent background lighting that is independent of external lighting conditions. Means of ventilation (not shown) may be provided to enable any hot air within the system 1 to be dissipated. Such means of ventilation include air vent, fans, etc., which should also be properly covered to prevent external light from entering the system 1.

The top section 3 houses a top imaging device 7, e.g. a surveillance camera, an automatic food dispenser, a mixing chamber and the inlet pipe (not shown) that supplies water from a source into a container 8. A customizable confinement structure 9 (to be described in detail below) is disposed within the container 8 in order to separate the aquatic organisms from accessories such as air stones, filter, thermostats, etc that are commonly found in aquariums but may not be relevant and indeed obstructive to the monitoring system of the example embodiment. A plurality of fish to be monitored are provided within the confinement structure 9. The confinement structure 9 comprises a substantially continuous perimeter wall for accommodating the fish therein, wherein and is dimensioned for accommodating a substantially 3-dimensional group behaviour of the fish. In addition, a plurality of ventilation holes (not shown) are provided on the confinement structure 9 to allow water, but not the fish, to pass through. The location of the automatic food dispenser is chosen such that any food dispensed will fall within the confinement structure 9 and the aquatic organisms can feed on it. The mixing chamber and inlet pipe can be located anywhere within the top section 3 as long as they do not obstruct the view of the top imaging device 7. An outlet pipe (not shown) is also provided for ensuring a continuous flow of water during monitoring. The top imaging device 7 may be adjusted by moving it physically or by adjusting its lens for capturing a top view of the confinement structure 9 for observing behavior of the fish therewithin.

The middle section 4 is separated from the lower middle section 5 by means of a separator 10. The separator 10 serves as a light diffuser to prevent excess light from entering the confinement structure area from below. It can be made of e.g. a large piece of light diffuser, or constructed using two pieces of acrylic sheet with a piece of semi-transparent paper sandwiched between them. The container 8 is disposed in the middle section 4 and rests on top of the separator 10. A speaker 16 is disposed adjacent to an external face of the container 8 to provide stimulus, e.g. a sound, to confirm whether a stationary fish is resting or dead (to be discussed in detail below).

A side imaging device 11 is mounted at a side of the enclosure 2 and is capable of capturing the side view of the fish within the confinement structure 9. The physical location and lens of the side imaging device 11 can be adjusted so that its field of view covers a region of the confinement structure 9 below the water surface. The lower middle section 5 houses a light box 12, which can be constructed e.g. by using fluorescence tubes. The length of the fluorescence tubes used is dependent on the size of the container 8, and the number of such tubes required is dependent on the surface area of the region to be illuminated. For a typical aquarium size of one foot by two feet, two fluorescence tubes of length two feet may be used. The bottom section 6 can be used to house various power switches, and as a place for storage. The enclosure unit 2 may be mounted on wheels, rollers, or any similar mechanism for ease of relocation.

Figure 1B:
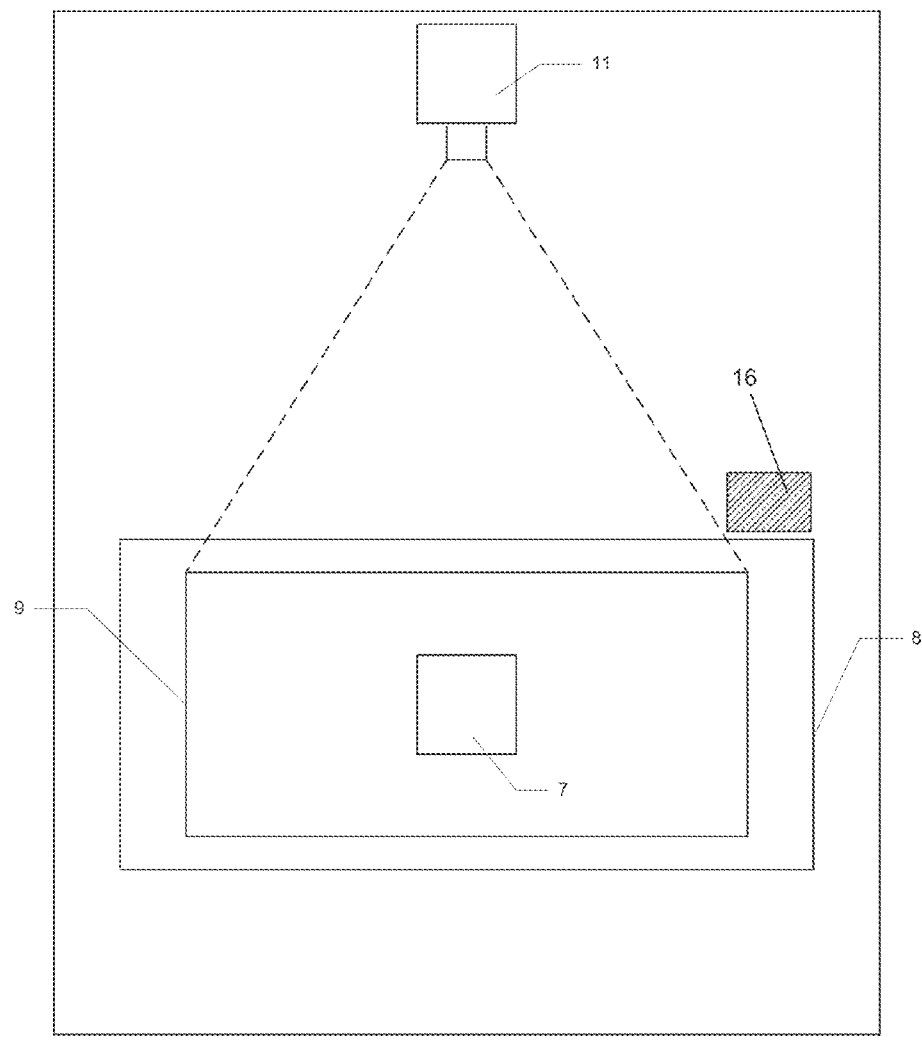
FIG. 1(b) is a top view of the system of FIG. 1(a).
Figure 1C:
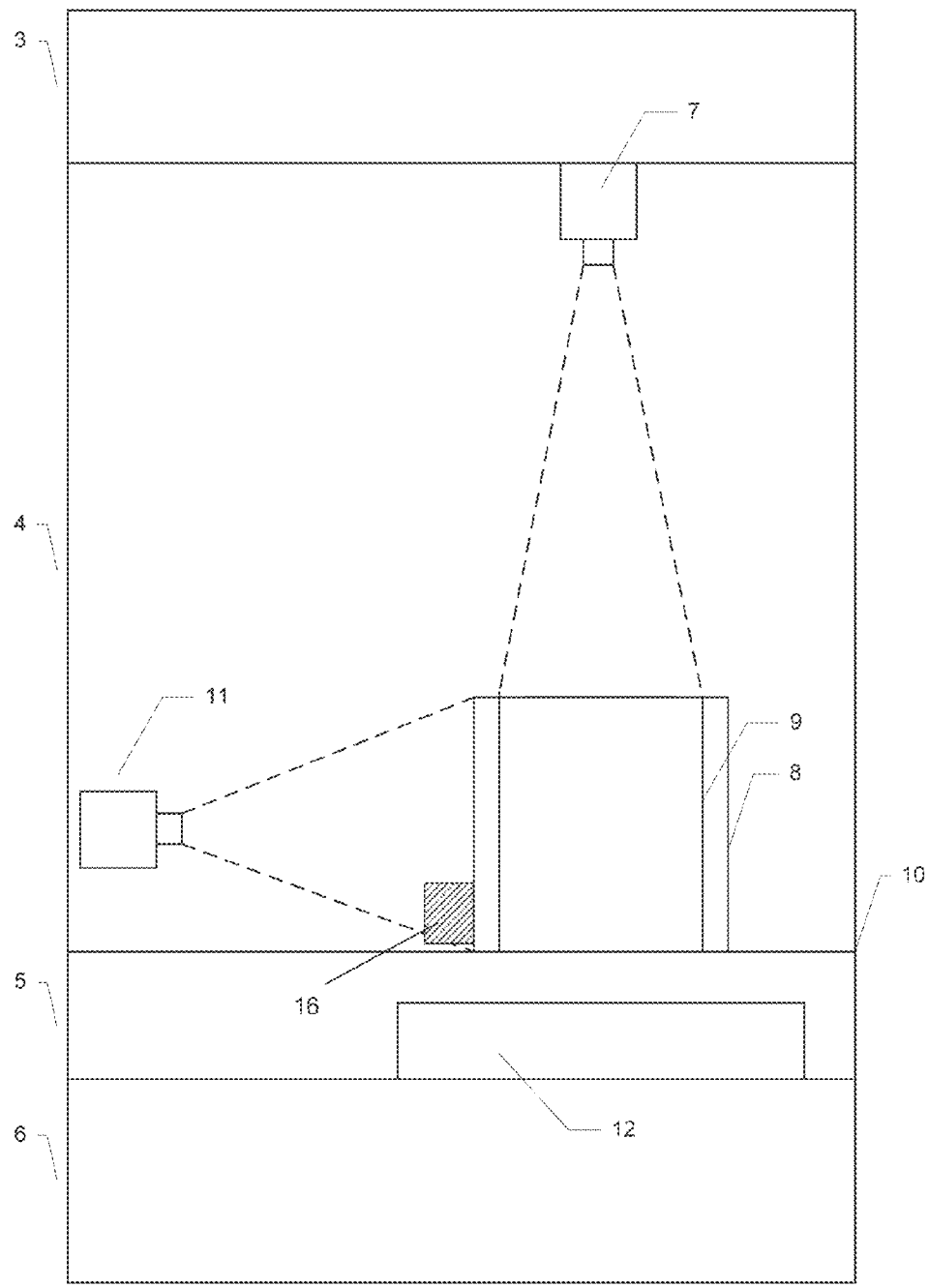
FIG. 1(c) is a side view of the system of FIG. 1(a).
Figure 1D:
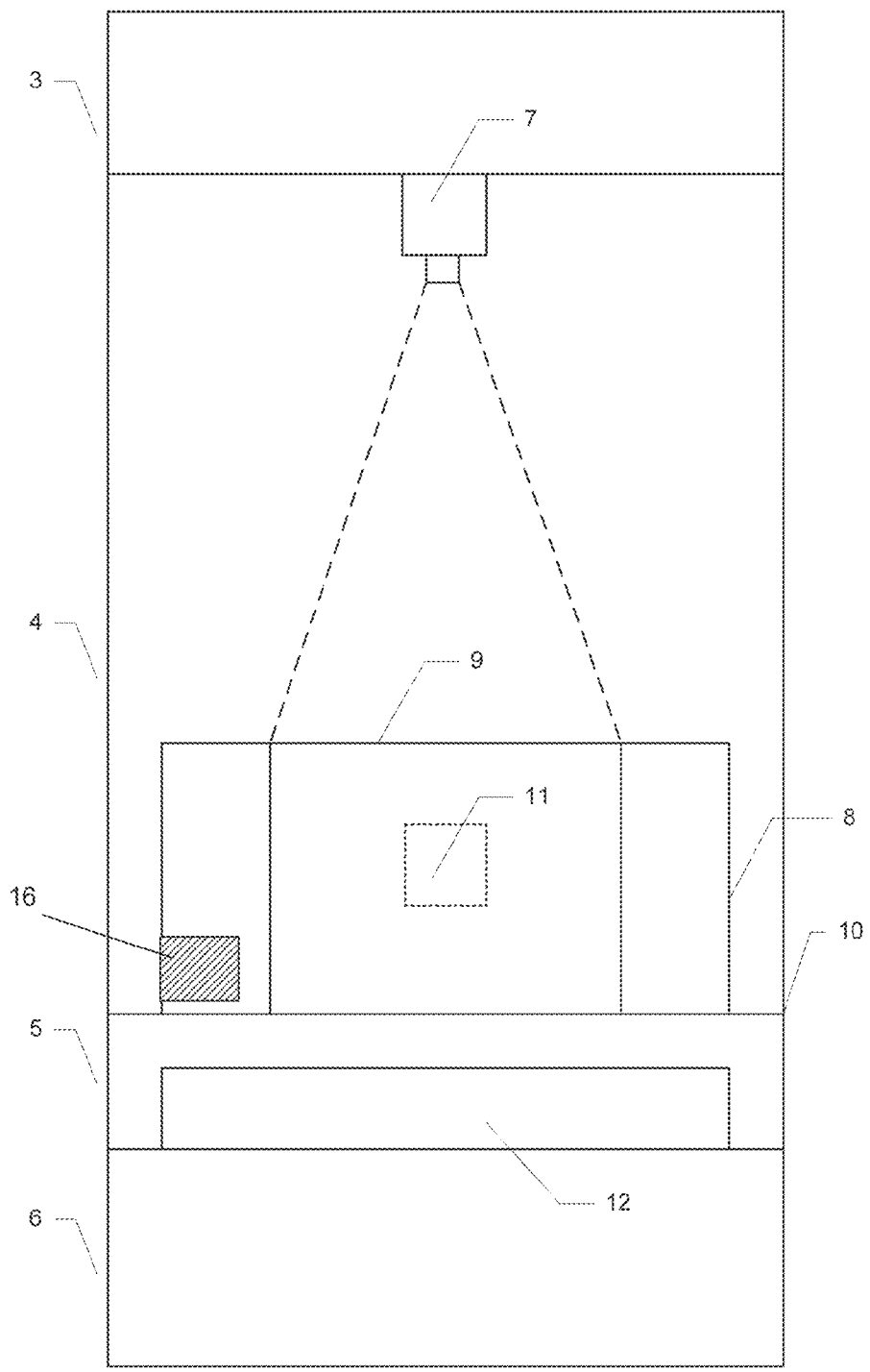
FIG. 1(d) is a front view of the system of FIG. 1(a).
Figure 2:
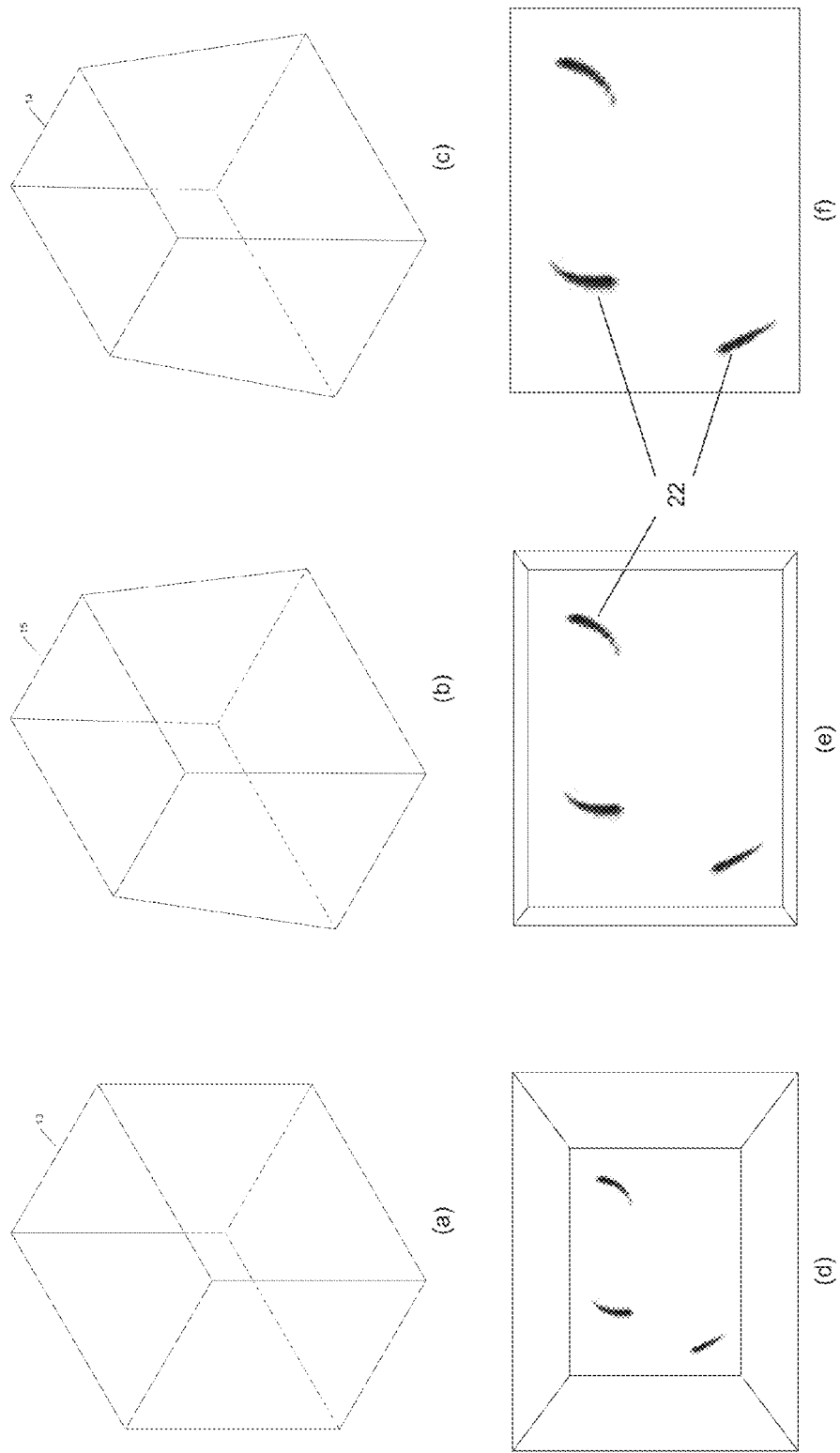
FIGS. 2(a)-2(c) show example embodiments of a confinement structure for use in the system of FIG. 1(a).
FIGS. 2(d)-2(f) show top views of a monitoring area using the confinement structure of FIGS. 2(a)-2(c) respectively.

Video data can be obtained from both the top imaging device 7 and the side imaging device 11 (FIG. 1(b)) in the example embodiment. It is desirable, that images captured by the top imaging device 7 provide as much detail as possible for distinguishing relevant features, while allowing for some adjustment, e.g. focusing. FIGS. 2(a)-2(c) show example embodiments of the confinement structure. FIGS. 2(d)-2(f) show top views of a monitoring area (as may be observed from the top imaging device 7) using the confinement structures of FIGS. 2(a)-2(c), respectively. The confinement structure is preferably made from a translucent material, e.g. matt clear acrylic, such that inner surfaces are matted or treated in a similar manner to reduce any potential reflection of the fish on the inner surfaces. In one embodiment with a rectangular-shaped confinement structure 13 (FIG. 2(a)), due to perspective, the view observed by the top imaging device 7 is limited by the boundary at the top of the confinement structure 13, as shown in FIG. 2(d), and the fish may appear relatively small.

In some situations, it is preferable to observe the fish at a higher detail level. FIG. 2(b) shows a confinement structure 15 having its sides disposed at a small angle to a vertical direction, while FIG. 2(c) shows a confinement structure 14 having its sides disposed at a larger angle to the vertical direction. Both confinement structures approximate a field of view of the imaging device 7, with confinement structure 14 being identical to the filed of view for a particular static set-up. As can be seen from FIGS. 2(e) and 2(f) respectively, the effect of perspective is largely eliminated in both cases. The top imaging device 7 is able to zoom in and the fish 22 appear larger as compared to the view in FIG. 2(d), hence more details can be observed. In addition, while the confinement structure 14 is ideal in providing the highest detail level, it requires that the specifications of the lens, location of the top imaging device 7, angle of confinement structure sides, etc. remain constant. As such, confinement structure 15 may be generally preferred as it allows slight adjustments to camera lens, camera position, and is therefore a more flexible design.

In embodiments in which both the top imaging device 7 and the side imaging device 11 are used, a side face of the confinement structure directly in front of the side imaging device 11 needs to be transparent for the side imaging device 11 to see the fish. In such embodiments, a rectangular confinement structure as shown in FIG. 2(a) may be preferred as the confinement structures shown in FIGS. 2(b)-2(c) may result in distorted images captured by side imaging device 11.

FIG. 3(a) shows a top view of a monitoring area using a rectangular confinement structure having a transparent side face according to an example embodiment. FIG. 3(b) shows a side view of a monitoring area using a rectangular confinement structure having a transparent side face according to an example embodiment. As shown FIG. 3(a), since the side face 18 is transparent, reflections 30 may be seen by the top imaging device 7, potentially misleading the system into overestimating the number of fish within the confinement structure. On the other hand, as shown in FIG. 3(b), no reflection is seen by the side imaging device 11 since the remaining side faces are matted as described above.

FIG. 3(c) is a perspective view of the confinement structure of FIG. 3(a) that has been modified to minimize reflection according to an example embodiment. FIG. 3(d) is a top view of the monitoring area using the confinement structure of FIG. 3(c). In the example embodiment, reflections can be minimized by tilting only the transparent side face. As can be seen from FIG. 3(c), side face 20 of confinement structure 19 is disposed at an angle to the vertical direction that is close to that of the viewing angle of the top imaging device 7. In addition, an opaque cover 21 may be placed at the top of the confinement structure 19. From FIG. 3(d), it can be seen that reflections are almost completely eliminated. It will be appreciated that in a preferred embodiment, the features of the opaque cover 21 may be employed with a confinement structure 14 or 15 (FIG. 2), to maintain an approximation of the field of view for the top imaging device 7 (FIG. 1b).

The system for monitoring water quality further comprises a computer system 800 as described above. Output from the top imaging device 7 is fed to the computer system 800 for further processing. System 1 further comprises communication and/or networking means to send an alert signal and/or video output to a remote location, e.g. to a monitoring office. It should be understood by a person skilled in the art that the system also comprises miscellaneous components such as a power supply, connecting cables, etc. for proper functioning.

With various components of system 1 set up and connected, the monitoring can be carried out automatically. In a first step of the monitoring process, foreground objects, e.g. fish, are detected based on background modeling and subtraction. As appreciated by a person skilled in the art, foreground in a scene is characterized by a relatively large deviation from background statistics. In the example embodiment, changes in the background of a scene are computed at every frame by comparing a current frame with respect to a background model. The background model may be calibrated separately beforehand based on a fully set up system with a clear background, i.e. without any fish. A similarity measure is computed between an incoming frame and the background using a normalized Mahalanobis distance in an example embodiment to provide an estimate of the similarity with respect to the background at every pixel. Thus, if a region of an image is sufficiently dissimilar from the background model, the regions may be considered a foreground object. A binary map is then formed for the current frame, in which regions corresponding to foreground objects are highlighted as motion blobs (i.e. silhouettes).

Figure 4:
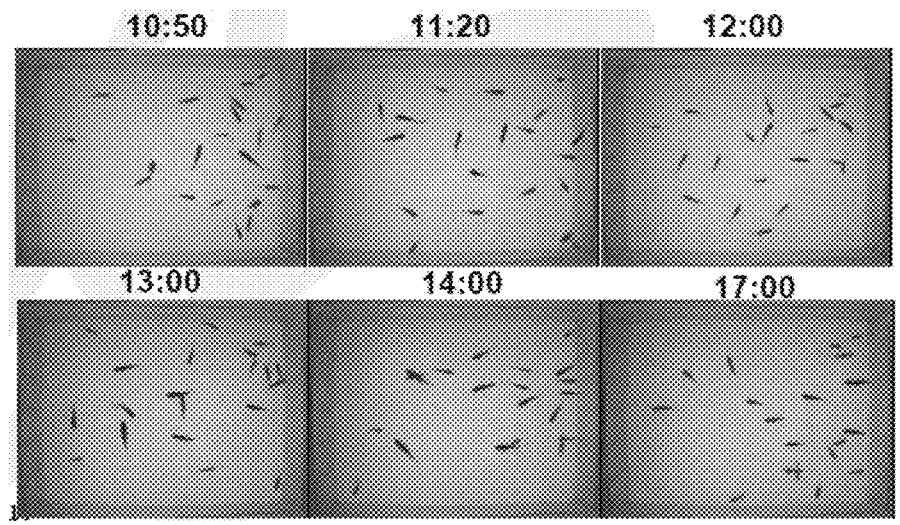
FIG. 4 shows results of foreground object detection over an extended period according to an example embodiment.

FIG. 4 shows results of foreground object detection over an extended period according to an example embodiment. The fish used for monitoring in the example embodiment comprise about 20 fish. However, it would be appreciated by one skilled in the art that a different number of fish can also be used. The detection results at various frames, as shown by different time marks, are consistent with the actual number of fish present in the images. Tracking of each individual object is performed by associating a current centroid of the respective blob to a projected centroid established based on a history file. The projection of centroids is performed by means of e.g. a Kalman filter or linear projection.

In the next step of the monitoring process, detected foreground objects are counted. Connected component labeling is applied in an example embodiment to group detected foreground pixels into components based on pixel connectivity, for object counting purpose. Pixels from the same blob are given the same label, and each blob is given a unique identity (ID). For a crowded scene, a higher level of complexity may be involved due to occlusions, i.e. events where silhouette masks of close foreground targets may overlap, resulting in formation of one or more contiguous blobs such that foreground objects may be clustered.

In the example embodiment, a blob splitting process is applied for resolving such occlusions. A blob is defined as a contiguous group of foreground pixels in the example embodiment. For example, a large blob may be observed when more than one fish come near to each other. The process according to the example embodiment is able to split the blob into separate ellipses where each ellipse represents one fish. Further, in the example embodiment, a "large size" threshold may be applied to remove very large blobs due to external subjects, e.g., a hand in the tank. Likewise, a "small size" threshold may be applied to remove noise pixels.

A silhouette map of a foreground object is viewed as a cluster of labeled foreground pixels where clustering and model-fitting concepts are deployed. A blob in frame t is denoted as $M^t$. Let $\gamma_i^t$ be a parameter vector characterizing an ellipse-shaped model for foreground i. The problem involves a process to identify a set of $\Gamma=\{\gamma_i^t\}$ such that this splits the blob into smaller ellipses, where each ellipse represents one fish. The problem can be formulated to maximize a posteriori given by:

$$\Gamma^{t*} = \operatorname{argmax} P(\Gamma^t \mid \Gamma^{t-1}, M^t) \quad (1)$$
$$\operatorname*{argmax}_{\Gamma^t} P(M^t \mid \Gamma^t) P(\Gamma^t \mid \Gamma^{t-1})$$

Further, the goodness of fitting $\gamma_i^t$ to $M^t$ may be measured by finding a solution $\gamma_i^t$ in the image lattice space that gives: i) a good coverage that includes as many considered foreground pixels but fewer background pixels, and ii) minimal overlapping between any two ellipse-shaped models for ensuring visibility of each ellipse.

Figure 5:
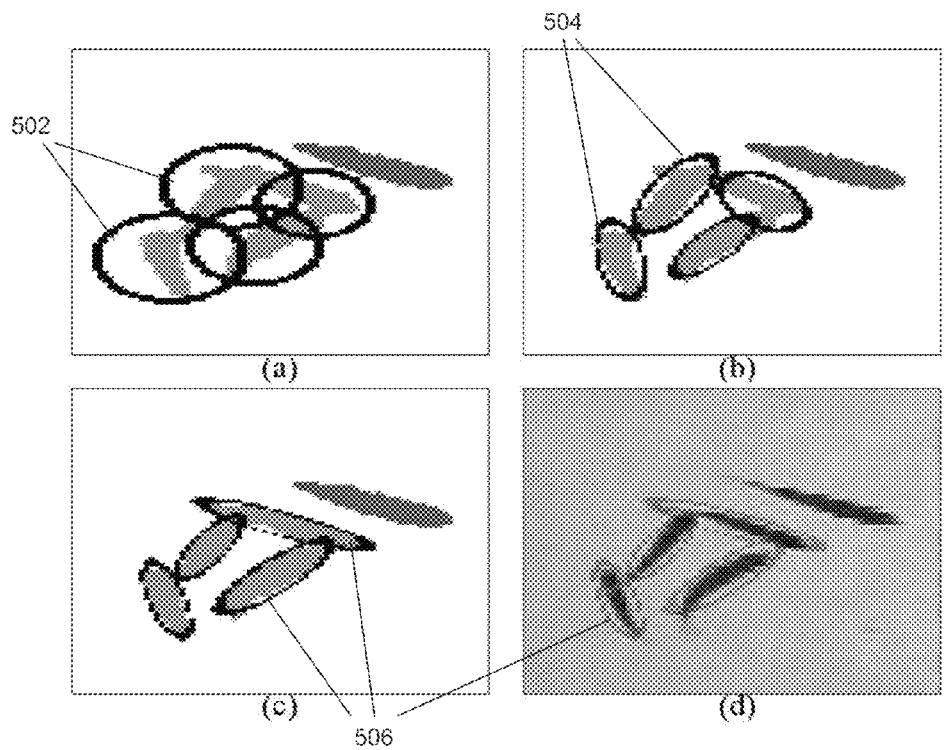
FIGS. 5(a)-5(d) show diagrams illustrating steps in a blob splitting process according to an example embodiment.

FIGS. 5(a)-5(d) show diagrams illustrating steps in a blob splitting process of the example embodiment. In an initialization step of the process, the blob $M^t$ is split into k smaller blobs. Hierarchical k-means clustering is performed on a data matrix comprising coordinates of foreground pixels. Let the number of cluster centers be k. As the clustering step comprises minimizing a function of spatial distances between cluster centers and foreground pixels, the step may yield cluster centers converging to the respective centroids of k objects, i.e. fitting k ellipses centered at the obtained cluster centers. A Euclidean distance may be used in the initialization step, thus giving an initial fitting with round-shaped models 502 as shown in FIG. 5(a).

With the obtained initial cluster centers, foreground pixels are classified and labelled to the respective nearest cluster center. The ellipse-model fitting can be improved by using a criterion that a Mahalanobis distance of a pixel to its nearest cluster center is less than a threshold. In the example embodiment, a threshold value of 1.8 has been applied; however, it should be appreciated that a higher or lower value may be used, depending on e.g. how elongated the fish are expected to be. The improved fitting in the form of elongated ellipses 504 are shown in FIG. 5(b).

In the next step of the blob splitting process, a best combination of ellipses is formed. The step starts by incrementing the value of k, which gives the number of ellipses to be formed. A recursive process is performed where parameters of k-number ellipses $\{\gamma_i\}$ are continuously adjusted to provide different likely hypotheses. A validity score defined based on a likelihood and prior components of Equation (1) is then computed for each hypothesis for selecting the best solution. The adjustment starts by re-labelling pixels of an ellipse i in the overlapping area to the next nearest ellipses j (j≠i, and j=1, . . . , k). As a result, ellipse i may shrink while other ellipses j may expand, thereby generating a new solution to the fitting. A likelihood and prior components may be computed to be:

$$P(M^t \mid \Gamma^t) \propto \sum_{i=1}^{k} \frac{A_{\gamma_i}^{bg} + A_{\gamma_i}^{ov}}{A_{\gamma_i}^{fg}}, \text{ and} \quad (2)$$

$$P(\Gamma^t \mid \Gamma^{t-1}, M^t) \propto \varphi |k^t = k^{t-1}|, \quad (3)$$

where $A_{\gamma_i}^{bg}$ and $A_{\gamma_i}^{fg}$ give the background and foreground pixel counts within the area defined by $\gamma_i^t$ respectively, $A_{\gamma_i}^{ov}$ gives the foreground pixel counts within the overlapping area of ellipse i and other ellipses, $k^t$ denotes the number of objects in the current frame and $k^{t-1}$ denotes the number of objects formed in the previous frame associated to $M^t$ in the current frame. Parameter ϕ serves as an empirical weight such that a higher value of ϕ is used to have more emphasis on the Equation (3) over Equation (2), and vice versa.

A validity score is computed as a product of (2) and (3). The above recursive process is then repeated for other values of i. The solution of $\{\gamma_i\}$ that corresponds to a minimum value of the computed validity score is recorded.

The adjustment of parameters and recording of computed validity score are repeated to continuously improve the fitting. As the recursive process is aimed at achieving a solution that gives a minimum value of the validity score, the process is terminated when the next validity score is greater than the current validity score. The end results shown in FIGS. 5(c)-5(d), i.e. ellipses 506 that closely model the respective individual silhouettes, correspond to the best performance for the case of a particular value of k.

In order to select the best value of k, the above steps of initialization and selection of best combination of ellipses are repeated for a range of k values, where the validity scores for the respective of k values is recorded, and the best k value is one that gives the minimum validity score.

Figure 6A:
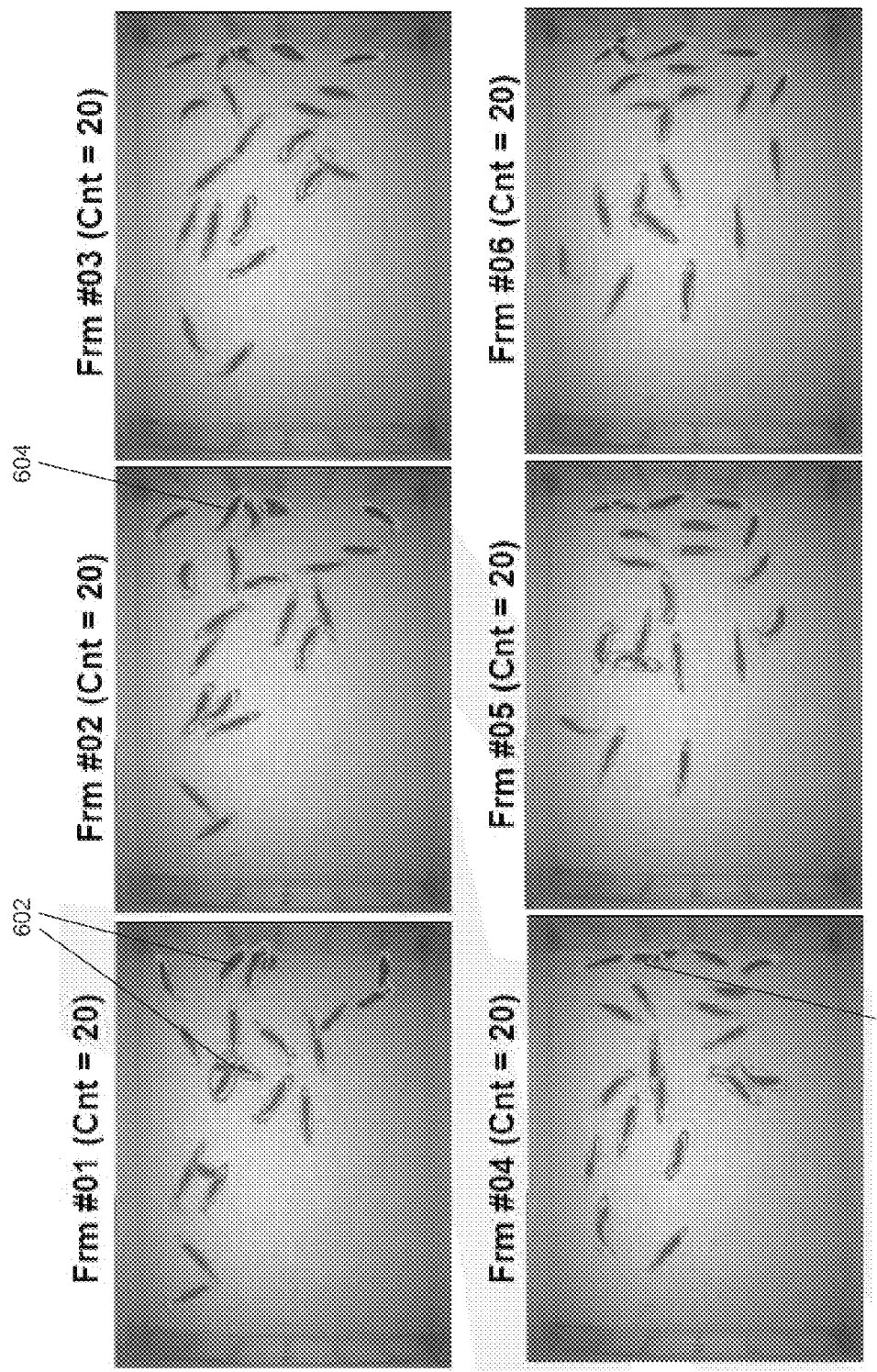
FIG. 6(a) shows results of the counting method according to an example embodiment at various frames.
Figure 6B:
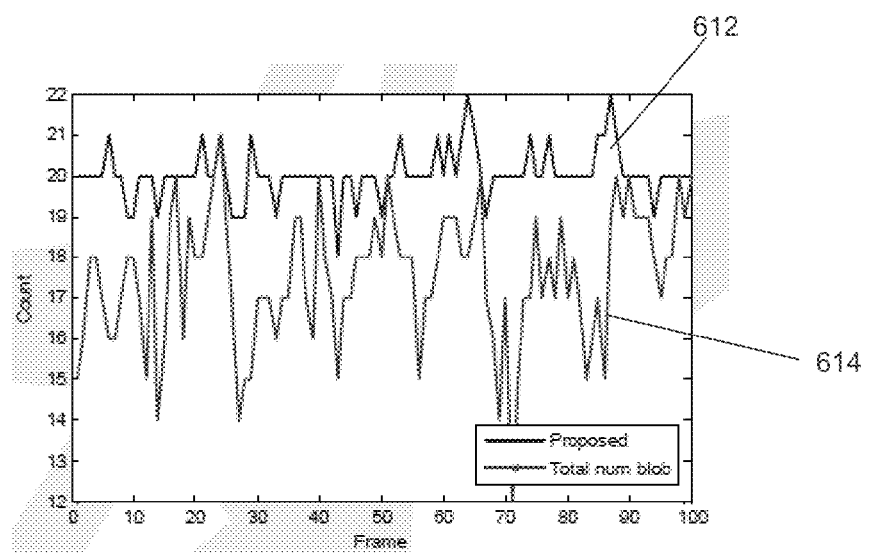
FIG. 6(b) shows a chart comparing performance of the counting method according to an example embodiment with a conventional method of counting number of blobs.

FIG. 6(*a*) shows results of the counting method according to the example embodiment in which 20 fish are being monitored at various frames. FIG. 6(*b*) shows a chart comparing performance of the counting method according to the example embodiment with a method of counting the original number of blobs, i.e. without applying the blob splitting. As can be seen from FIG. 6(*a*), example occlusions 602, 604, 606 are successfully resolved and the count number remains steady at the various frames. Further, from FIG. 6(*b*), the counting method of the example embodiment, as represented by line 612, provides relatively consistent results over time and shows little fluctuation in the count number, while the conventional method, as represented by line 614, gives significantly more false counts and greater fluctuation. It has been found in an example experiment that the counting method of the example embodiment has a mean error of 0.31 and a standard error of 0.6093 while the corresponding values for the conventional method of counting number of blobs are 2.48 and 0.6540 respectively.

Figure 7:
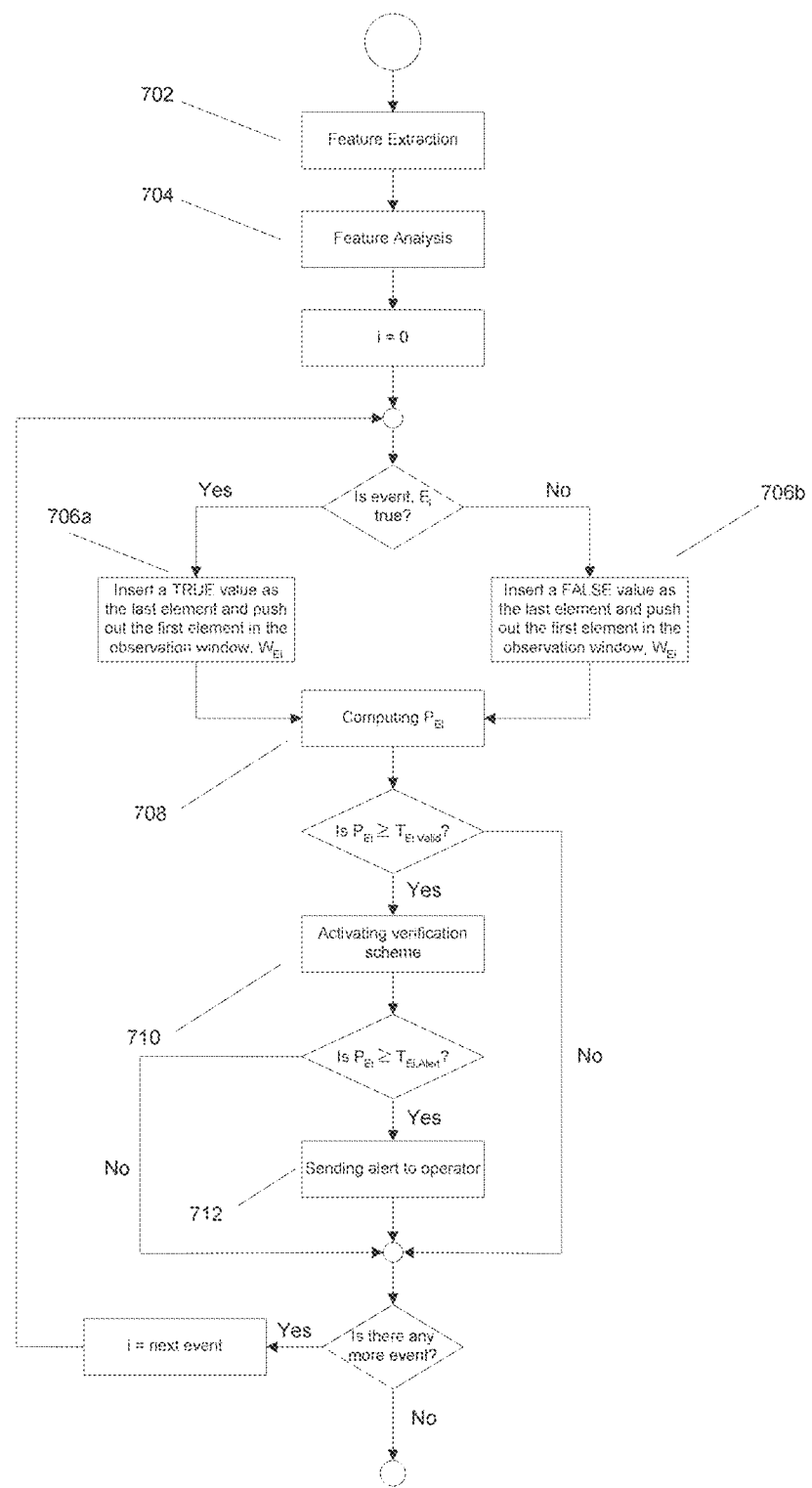
FIG. 7 shows a block diagram illustrating a method for analysing activity of test organisms for triggering an alert to an operator according to an example embodiment.

In a next step of the monitoring process, the activity of fish are analysed for alert triggering. FIG. 7 shows a block diagram illustrating a scheme for analysing activity of fish for triggering an alert to an operator according to an example embodiment. At step 702, relevant features such as spatial location of the centroid, body orientation and size, etc. of the fish are extracted once the fish are successfully tracked. In addition, from the temporal domain of the above, other features such as rate of orientation change, moving direction and regularity of motion may also be obtained. From the analysis, an inactive and thus potentially dead fish is determined in the example embodiment based on one or more of a group of detection of a motionless fish based on a motionless centroid/ellipse, side-ways oriented fish based on changes in the form of the ellipse from substantially elongate to substantially round, and fish floated to the top based on image data captured by the side imaging device.

At step 704, the extracted features are analysed. Furthermore, to take into consideration where monitored targets may be at rest or asleep for certain period of time in a continuous monitoring process, the system according to the example embodiment is able to tolerate a certain degree of inactiveness of the fish in order to minimize false alarm rate. In the example embodiment, about 20 fish are used, and a two-stage verification scheme is implemented. A set of events $\{E_1, \ldots, E_N\}$ is denoted as events of interest. For example, $E_5$ represents the event where at least 5 inactive fish are detected.

Starting with i=1, in the first stage, within each observation window $W_{Ei}$, if event $E_i$ occurs, a TRUE value is inserted as the last element in the observation window $W_{Ei}$ and the first element in the observation window $W_{Ei}$ is removed (step 706*a*); otherwise, a FALSE value is inserted as the last element in the observation window $W_{Ei}$ and the first element in the observation window $W_{Ei}$ is removed (step 706*b*). At step 708, an occurrence percentage $P_{Ei}$ for event $E_i$ is computed for the observation window $W_{Ei}$.

In the example embodiment, two thresholds, $T_{Ei,Valid}$ and $T_{Ei,Alert}$, where $T_{Ei,Valid} < T_{Ei,Alert}$ are used. At step 710, a verification scheme is activated if $P_{Ei} > T_{Ei,Valid}$, i.e. the occurrence percentage for event $E_i$ exceeds the lower threshold. Otherwise, the process restarts to step 702. For the verification scheme, a sound may be generated from the speaker 16 (FIGS. 1(*b*)-1(*d*)) for alerting the fish, which are known to be sensitive to sounds. It should be appreciated that other means, e.g. vibration, for alerting the fish may also be used.

If the inactive fish start moving after the sound is generated, the value of $P_{Ei}$ in the next frames may drop such that it is smaller than the lower threshold $T_{Ei,Valid}$ and the sound is turned off. This suggests that the inactive fish may have been resting or sleeping initially, and the monitoring continues normally. If the event $E_i$ is still observed in the next frames after the sound is generated, the value of $P_{Ei}$ may eventually exceed the upper threshold $T_{Ei,Alert}$. It is likely that the inactive fish are dead and an alert is sent to an operator (step 712). The alert may be sent in the form of audio and/or video with a text message to state the event and the location for necessary actions to be taken. It can be transmitted via the communication and/or networking means as described above using wired or wireless communication to a receiving device at a remote location. If there is no further event, the process restarts for the next frame at step 702; otherwise, the next event, e.g. $E_{i+1}$, is analysed.

It will be appreciated by a person skilled in the art that the values for the above thresholds can be set appropriately to optimise the responses in steps 710 and 712. An example range is about 0.75 to 0.85 in one embodiment.

Figure 9:
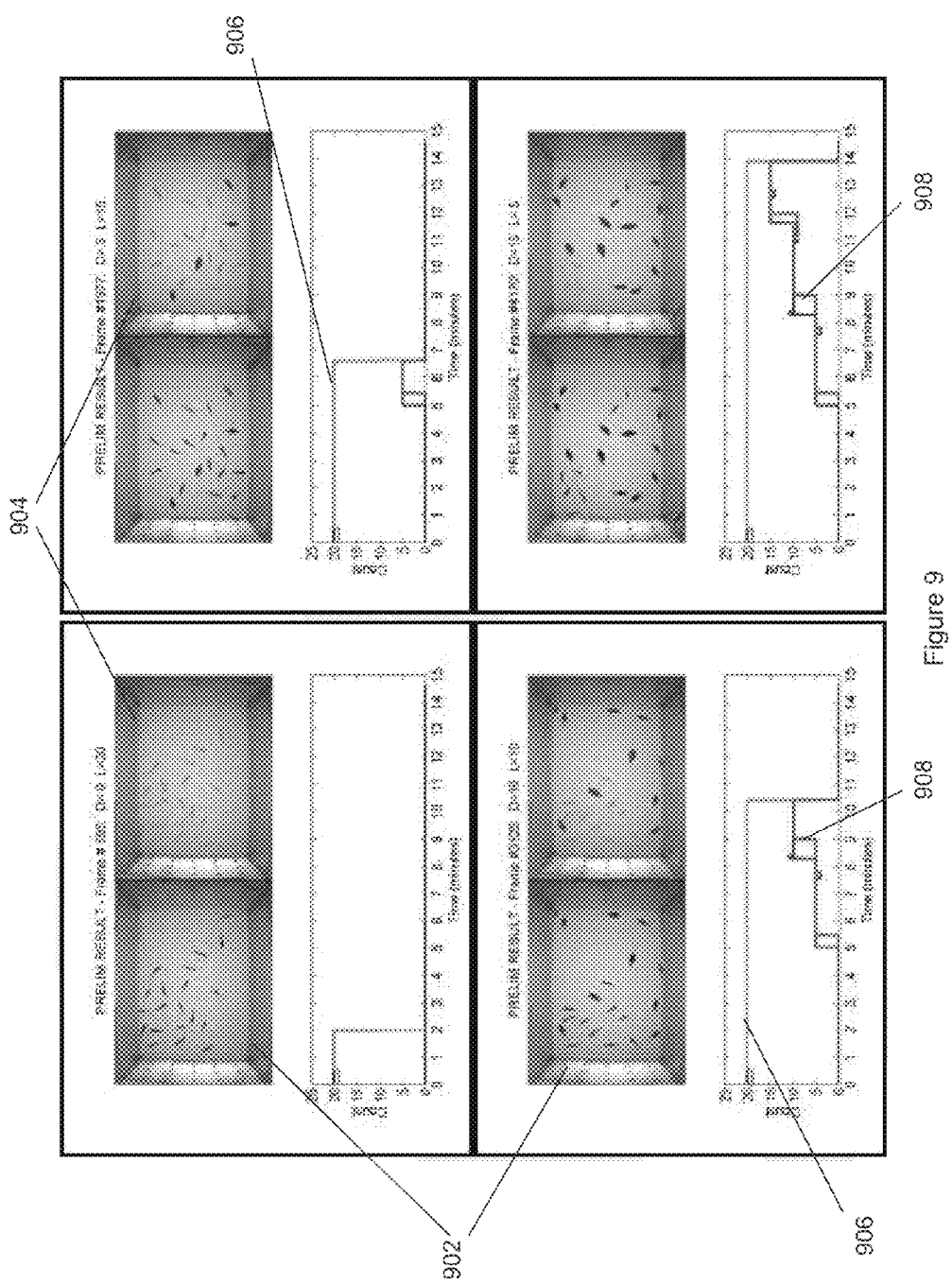
FIG. 9 shows images obtained at different points over an interval, the corresponding foreground detection results and number of inactive organisms counted, according to an example embodiment.

Experiments have been conducted to verify the system and method of the example embodiment. FIG. 9 shows images 902 obtained at different points over an interval, the corresponding foreground detection results 904 and number of inactive fish counted from one of the experiments. In the example experiment, the monitoring starts with 20 live fish. It is followed by adding 5 dead fish while removing 5 live fish each time until the numbers of live and dead fish in the container become 5 and 15, respectively. As can be seen from FIG. 9, the total number of foreground objects detected, as represented by line 906, remains constant over the entire interval. The number of inactive fish counted, as represented by line 908, show step-wise increases corresponding to each time the dead fish are added and live fish removed, indicating that the system is responsive to changes.

As an alternative or in addition to the counting of inactive fish as described above, the system of the example embodiment is also capable of early detection of abnormal fish behaviour. In the description that follows, the behaviour of a school of fish may be quantified as one or more of a group consisting of:

activity level,
school distribution, and
social interaction.

In the example embodiment, images are captured at about six frames per second. However, it should be appreciated that a different number of frames per second can also be used. A tracking module is used to associate the same fish throughout the image sequence. Using the spatial information provided by its physical dimension and position mapped on the images, each fish i can be represented by a set of coordinates of the pixels which it occupies.

$$F_i = \begin{Bmatrix} (x_1, y_1) \\ (x_k, y_k) \\ \ldots \\ (x_S, y_S) \end{Bmatrix} \quad (4)$$

where $F_i$ is the representation fish i, $(x_k, y_k)$ is the coordinate for the $k^{th}$ pixel occupied by the fish and S is the total number of pixels occupied by the fish.

Further, in the example embodiment, features such as position and size, as represented by a pair of coordinates $(P_x, P_y)$ of the centroid of each fish in the image and the total number of pixels S being occupied by each fish in the image respectively, can be computed based on the above coordinate information.

Activity Level

The activity level of the fish school in the example embodiment can be determined by how fast the fish swim and the complexity of their swimming path. The speed of each fish in the confinement area can be calculated by taking the displacement of its position between consecutive frames. The overall group speed can be computed by:

$$v = \Sigma \sqrt{(P_x(t)-(P_x(t-1))^2+(P_y(t)-P_y(t-1))^2} \qquad (5)$$

where $P_x(t)$ and $P_y(t)$ represent the x and y coordinates of the position of a fish (as represented by its centroid) at Frame t, and $P_x(t-1)$ and $P_y(t-1)$ represent the x and y coordinates of the position of the same fish at Frame t−1.

Figure 10:
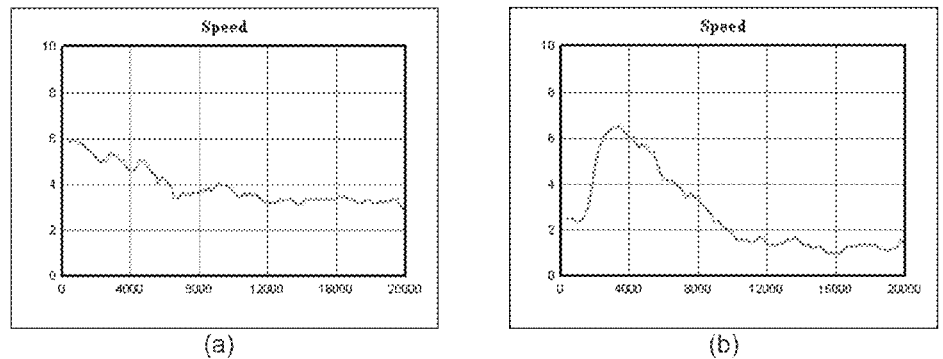
FIGS. 10(a) and 10(b) show graphs of comparative overall school speed over about 20,000 frames according to an example embodiment.

FIGS. 10(a) and 10(b) show graphs of the overall school speed for a control tank (Tank A) and a test tank (Tank B), respectively, over about 20,000 frames according to an example embodiment. The conditions, e.g. size of confinement structure, lighting, type of number of fish used, etc. for both tanks are identical, except that the water in the test tank (Tank B) is contaminated with e.g. Chlorine. The fish are put into the water at Frame 0. It can be seen that the speed of the fish in Tank A becomes relatively stable after the fish have settled down at around Frame 6000. This is different from the results for Tank B where the fish show relative hyperactivity after being placed into the tank and start to swim more lethargically after a while. A lower speed may indicate difficulties in swimming imposed by the chemical contamination in the water.

Figure 11:
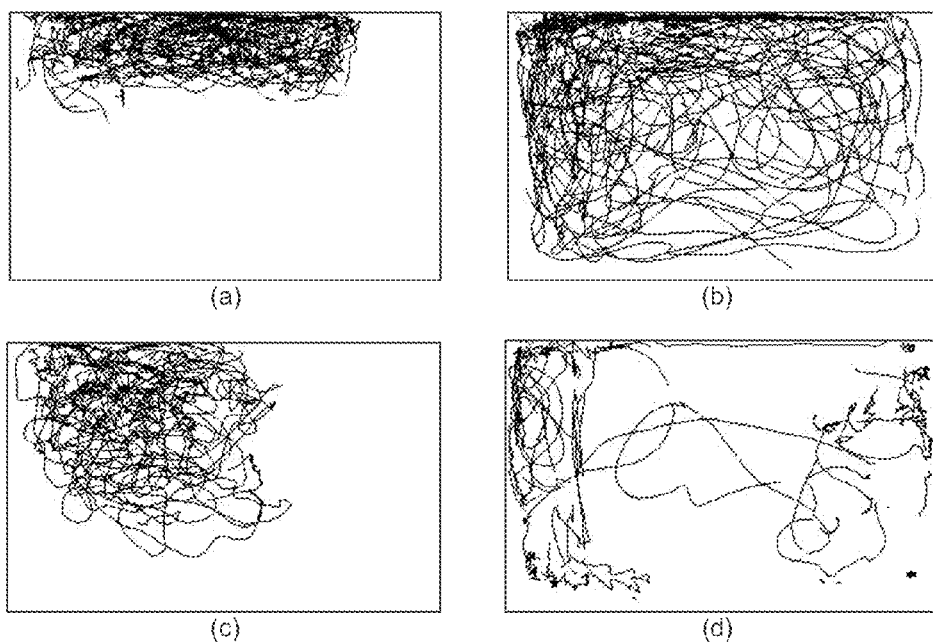
FIGS. 11(a) and (b) show comparative motion trajectories of the fish between Frame 2,001 and Frame 2,250 of FIG. 10.
FIGS. 11(c) and (d) show comparative motion trajectories of the fish between Frame 19,751 and Frame 20,000 of FIG. 10.

The results can be verified by analysing the motion trajectory (i.e. swimming path) of the fish. FIGS. 11(a)-(d) show diagrams displaying the swimming paths of e.g. 20 fish over about 250 frames for the two tanks at two instances. FIGS. 11(a) and (b) show the motion trajectories of the fish in Tank A and Tank B respectively between Frame 2,001 and Frame 2,250 according to an example embodiment. FIGS. 11(c) and (d) show the motion trajectories of the fish in Tank A and Tank B respectively between Frame 19,751 and Frame 20,000 according to an example embodiment.

As seen in FIG. 11(b), the messy and complex trajectory in Tank B seem to indicate an erratic behaviour, which may correspond to the rise in speed between Frame 2,001 and Frame 2,250. As the fish start to swim slower between Frame 19,751 and 20,000, a less dense trajectory, which mostly occupies the sides of the tank, can be seen in FIG. 11(d). On the other hand, as shown in FIGS. 11(a) and (c), the fish in Tank A swim in a more controlled and regular manner.

Furthermore, in the example embodiment, based on the obtained motion trajectory, a randomness measure of fish activity can be computed by:

$$\text{Randomness} = \frac{\text{Size of trajectory}}{v} \qquad (6)$$

where the size of trajectory may be computed based on the area covered by an average motion trajectory over a given time.

Figure 12:
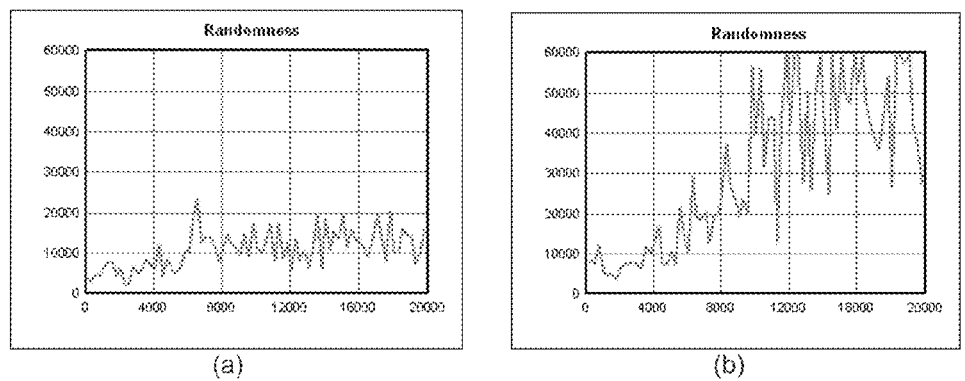
FIGS. 12(a) and (b) show graphs of comparative randomness measures over the about 20,000 frames of FIG. 10.

FIGS. 12(a) and (b) show graphs of the randomness measure for Tank A and Tank B of FIGS. 10(a) and (b) respectively according to an example embodiment. It can be seen from FIGS. 12(a) and 12(b) that the activity level of the fish in the contaminated container (Tank B) is higher and more erratic than that in the control tank (Tank A) which seems to be more consistent.

School Distribution

The distribution of a fish school is determined in the example embodiment by the population of fish in different parts of the confinement structure. First, the monitoring area of the confinement structure is split into more than one region. This is followed by the calculation of occupancy Q in each region, which may be represented by the percentage of the size of fish in that region over the total fish size for the whole confinement structure:

$$Q = \frac{\sum_{j=1}^{r} S_j}{\sum_{i=1}^{n} S_i} \times 100\% \qquad (7)$$

where $S_j$ is the size of fish j located in the region, and r the number of fish located in the same region, while $S_i$ is the size of fish i and n the total number of fish in the confinement structure.

Avoidance behaviour has been observed in fish where water in the container is contaminated. Hence, the system of the example embodiment makes use of Q to determine if there is any region in the confinement structure where the fish are trying to swim away from or attracted to. Also, fish are observed to swim along the sides of the confinement structure when there is an alteration in the water condition in some cases. In the example embodiment, the regions can be defined by splitting the monitoring area into e.g. a centre region and a side region.

Figure 13:
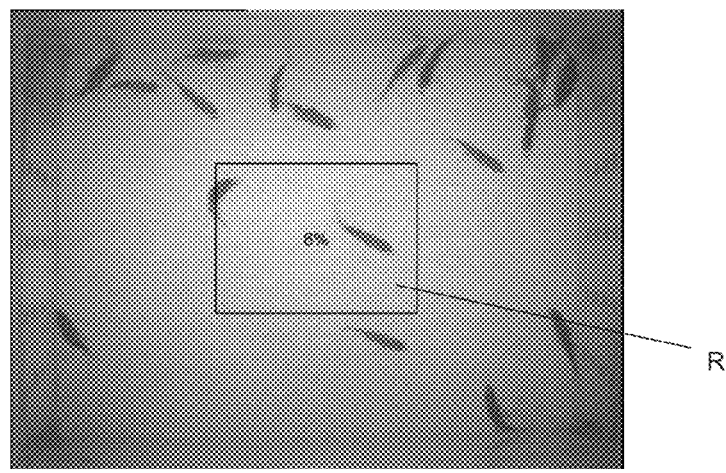
FIG. 13 shows a top view of the confinement structure illustrating a centre monitoring region according to an example embodiment.

FIG. 13 shows a top view of a monitoring area of the confinement structure defining a centre region R according to an example embodiment. As can be seen from FIG. 13, the boundary between the centre region R and the side region is marked e.g. by a rectangle, and the number stated at the centre is the occupancy in the centre region R. For example, in this view, about 8% of the total fish size is detected in the centre region R. Further, for each frame, the occupancy value is compared to a threshold, T, for determining if the probability of avoidance behaviour, Pb(t), would increase.

$$Pb(t) = \begin{cases} (1-\alpha)Pb(t-1) + \alpha, & Q < T \\ (1-\alpha)Pb(t-1), & Q \geq T \end{cases} \qquad (8)$$

where $\alpha$ is the weight of each frame and, Pb(t) and Pb(t−1) are the computed probabilities at Frames t and t−1 respectively.

The monitoring of group distribution in the confinement structure may help to identify avoidance behaviour, which the fish may exhibit when there is a disturbance in a certain region of the confinement structure. In the example embodiment, the probability of avoidance behaviour is calculated over a specified number of frames, with each frame having the same weightage, and the probability would increase if the percentage of fish found in the monitored region is less than a certain level, i.e. if most of the fish school is swimming along the sides of the confinement structure, the probability of avoiding the centre region will increase as Q for the centre region is less than T.

Figure 14:
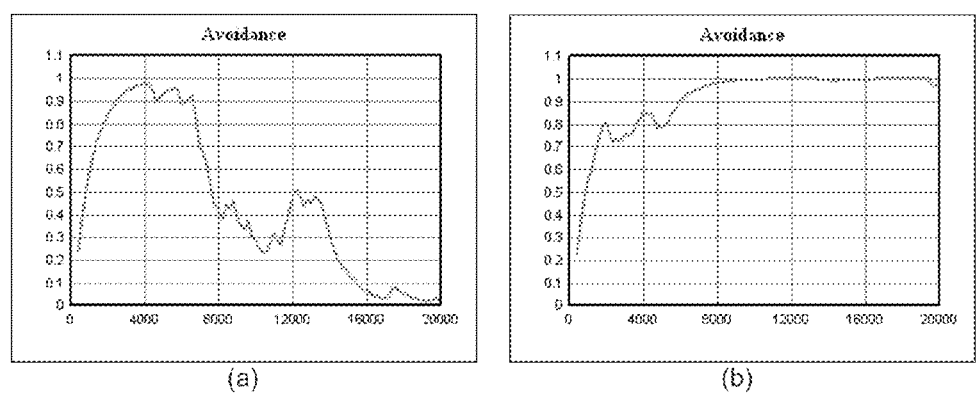
FIGS. 14(a) and 14(b) show graphs of comparative probability of avoidance behaviour over a period of about 20,000 frames according to an example embodiment.

FIGS. 14(a) and 14(b) show graphs comparing of the probability of avoidance behaviour for a control tank (Tank A) and a test tank (Tank B) respectively over a period of time (about 20,000 frames) according to an example embodiment. As can be seen from FIGS. 14(a) and (b), there is a significant difference in the results obtained from the two tanks. The probability of avoidance behaviour in Tank B remains high even when the fish in Tank A seem to be settled down in the new environment. This may indicate that the contaminant in Tank B affects the distribution of the fish school within the tank as the fish seem to be swimming away from the centre region.

Social Interaction

The social interaction among the fish may be defined in the example embodiment by one or more of e.g. the level of proximity that the fish are swimming to one another, the number of clusters formed by the fish school and dominance of these clusters, and the presence of leaders in the group.

In the example embodiment, the hierarchical k-means clustering method is used to perform clustering iterations on images of the fish. The process makes use of the coordinates obtained from the positions of the fish. When any fish is too far from the centre of the school, a cluster is formed. The number of clusters may keep on increasing until one of the following predetermined conditions is met:

The distance between the centroid of every fish and the centre of the cluster it belongs to is within a specified length, i.e.

$$\sqrt{(P_x - N_x)^2 + (P_y - N_y)^2} < T_C$$

The density of the fish is more than a specified percentage, i.e.

$$D = \frac{\sum_{i=1}^{c} S_i}{A} > \beta$$

where N is the cluster centre, A is the area of the convex hull representing a cluster, c is the number of fish belonging to the same cluster, and $T_c$ and $\beta$ are pre-defined thresholds respectively.

Figure 15A:
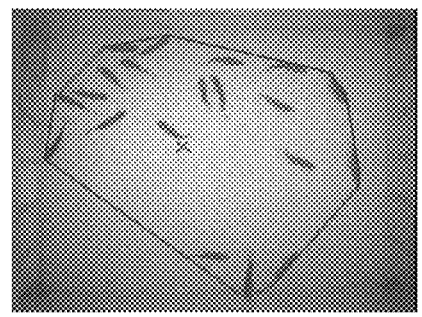
FIG. 15(a) shows a top view of the monitoring area of the confinement structure with one cluster of fish fitted according to an example embodiment.
Figure 15B:
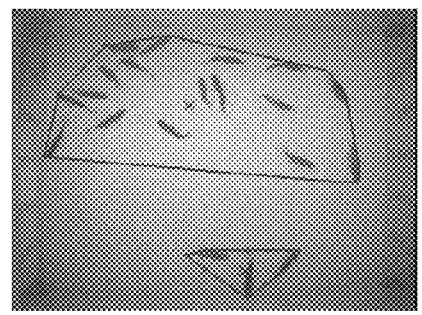
FIG. 15(b) shows the same top view as FIG. 15(a) with two clusters of fish fitted according to an example embodiment.

FIG. 15(a) shows a top view of the monitoring area of the confinement structure with one cluster of fish. FIG. 15(b) shows the same top view as FIG. 15(a) with two clusters of fish. As can be seen from FIGS. 15(a) and 15(b), the number of clusters (i.e. when the iteration stops) for the same image is dependent on the values of the thresholds, e.g. the density threshold in FIG. 15(a) is lower than that in FIG. 15(b).

After the clusters are formed, the majority cluster in the school may be identified in the example embodiment by computing the size of every cluster, which is equivalent to the sum of size S of the fish that belong to the same cluster. The cluster with the largest size is then labelled as the majority. The size of the majority cluster is then plotted as a percentage of the total school size over a specified number of frames for the fish in both control and contaminated tanks.

Figure 16:
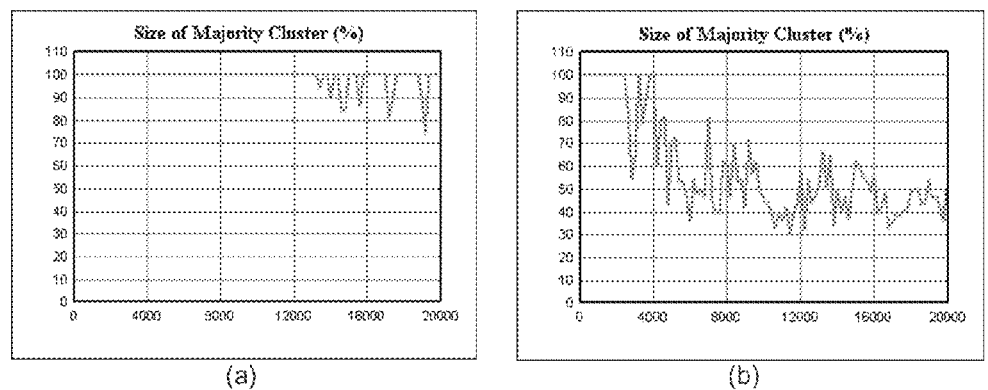
FIGS. 16(a) and 16(b) show graphs of comparative size of majority cluster data over a period of about 20,000 frames according to an example embodiment.

FIGS. 16(a) and 16(b) show graphs comparing the size of the majority cluster for a control tank (Tank A) and a test tank (Tank B) respectively over a period of time (about 20,000 frames) according to an example embodiment. The graphs show that the fish school in contaminated water tends to be more scattered, as may be indicated by smaller majority cluster size, compared to that in a normal water condition.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A system for monitoring water quality, the system comprising:
    a container for receiving a flow of water to be monitored, the container being configured for containing a plurality of fish and for accommodating a substantially 3-dimensional group behaviour of the fish;
    a first imaging device disposed above the container for obtaining top view video data of the fish; and
    means for identifying individual fish based on foreground object detection,
    wherein the means for identifying individual fish is arranged for resolving clustered foreground objects.

2. The system as claimed claim 1, further comprising a second imaging device disposed on a side of the container for obtaining side view video data of the fish.

3. The system as claimed in claim 1, further comprising a confinement structure disposed within said container, the confinement structure comprising a substantially continuous perimeter wall for accommodating the fish therein, wherein said confinement structure is dimensioned for accommodating the substantially 3-dimensional group behaviour of the fish.

4. The system as claimed in claim 3, wherein the perimeter wall is configured such that it approximates a field of view of said first imaging device.

5. The system as claimed in claim 4, wherein the perimeter wall is substantially translucent.

6. The system as claimed in claim 4, wherein a portion of the perimeter wall facing said second imaging device is substantially transparent, while a remaining portion of the perimeter wall is substantially translucent.

7. The system as claimed in claim 6, wherein the confinement structure further comprises a substantially opaque cover member disposed to cover the substantially transparent portion of the perimeter wall for reducing reflection of the fish in said top view video data.

8. The system as claimed in claim 1, further comprising a lighting apparatus configured to provide substantially even background light for the first imaging device.

9. The system as claimed in claim 8, wherein the lighting apparatus comprises a light source disposed underneath the container and means for diffusing light from the light source disposed between the light source and the container.

10. The system as claimed in claim 1, wherein the system is configured to minimize external light from entering the system during operation.

11. The system as claimed in claim 1, wherein resolving clustered foreground objects comprises:
    performing hierarchical k-means clustering to fit k-number of ellipses into each contiguous blob in a silhouette map of the top view image data, k=1, 2, 3, ...;
    determining a best k based on a minimum validity score for fitting the k-number of ellipses to each blob.

12. The system as claimed in claim 1, further comprising means for determining a number of inactive fish.

13. The system as claimed in claim 12, wherein the means for determining the number of inactive fish extracts one or more features of a group consisting of location of centroid, body orientation and size, rate of orientation change, moving direction and regularity of motion for determining if a fish is inactive.

14. The system as claimed in claim 12, further comprising means for applying a stimulus to the fish if the number of inactive fish exceeds a first threshold to reduce false alarms.

15. The system as claimed in claim 14, further comprising a communication device for sending an alarm signal, the alarm signal being generated if the number of inactive fish exceeds a second threshold after the stimulus has been applied.

16. The system as claimed in claim 14, wherein the stimulus comprises a sound.

17. The system as claimed in claim 1, further comprising means to determine an activity level of the plurality of fish as a group behaviour, the activity level being determined based on one or more of a group consisting of overall group speed, motion trajectory and randomness measure.

18. The system as claimed in claim 1, further comprising means to determine a group distribution of the fish as a group behaviour.

19. The system as claim in claim 1, further comprising means to determine a social interaction of the fish as a group behaviour, the social interaction being determined based on one or more of a group consisting of level of proximity that the fish are swimming to one another, number of clusters formed by the fish and dominance of these clusters.

20. A method of monitoring water quality, the method comprising the steps of:
receiving a flow of water to be monitored in a container, the container being configured for containing a plurality of fish and for accommodating a substantially 3-dimensional group behaviour of the fish;
obtaining top view video data of the fish; and
identifying individual fish based on foreground object detection,
wherein identifying individual fish comprises resolving clustered foreground objects.

21. The method as claimed claim 20, further comprising:
performing hierarchical k-means clustering to fit k-number of ellipses into each contiguous blob in a silhouette map of the top view image data, k=1, 2, 3, . . . ;
determining a best k based on a minimum validity score for fitting the k-number of ellipses to each blob.

22. The method as claimed in claim 20, further comprising applying a stimulus to the fish if a number of inactive fish exceeds a first threshold to reduce false alarms.

23. The method as claimed in claim 20, further comprising determining an activity level of the plurality of fish as a group behaviour, the activity level being determined based on one or more of a group consisting of overall group speed, motion trajectory and randomness measure.

24. The method as claimed in claim 20, further comprising determining a group distribution of the fish as a group behaviour.

25. The method as claim in claim 20, further comprising determining a social interaction of the fish as a group behaviour, the social interaction being determined based on one or more of a group consisting of level of proximity that the fish are swimming to one another, number of clusters formed by the fish and dominance of these clusters.

* * * * *